US012357270B2

(12) United States Patent
Tisa et al.

(10) Patent No.: US 12,357,270 B2
(45) Date of Patent: Jul. 15, 2025

(54) BIMODAL ULTRASONIC PROBE COMPRISING AN OPTICAL DEVICE FOR DIAGNOSIS

(71) Applicants: Micro Photon Devices Srl, Bolzano (IT); VERMON S.A., Tours (FR); COMMISSARIAT A L'ENERGIE ATOMIQUE ET AUX ENERGIES ALTERNATIVES, Paris (FR); POLITECNICO DI MILANO, Milan (IT)

(72) Inventors: Simone Tisa, Segrate Mi (IT); Alessandro Ruggeri, Fiorano al Serio BG (IT); Bogdan Rosinski, Langeais (FR); Emmanuel Montauban, Joue-les-Tours (FR); Jean-Marc Dinten, Grenoble (FR); Antonio Pifferi, Milan (IT); Paola Taroni, Como (IT); Alberto Dalla Mora, Fiorenzuloa d'Arda (PC) (IT); Alberto Tosi, Paruzzaro (IT)

(73) Assignees: Micro Photon Devices Srl, Bolzano (IT); VERMON S.A., Tours (FR); COMMISSARIAT A L'ENERGIE ATOMIQUE ET AUX ENERGIES ALTERNATIVES, Paris (FR); POLITECNICO DI MILANO, Milan (IT)

( * ) Notice: Subject to any disclaimer, the term of this patent is extended or adjusted under 35 U.S.C. 154(b) by 891 days.

(21) Appl. No.: 17/436,387

(22) PCT Filed: Mar. 3, 2020

(86) PCT No.: PCT/FR2020/050423
§ 371 (c)(1),
(2) Date: Feb. 23, 2022

(87) PCT Pub. No.: WO2020/178522
PCT Pub. Date: Sep. 10, 2020

(65) Prior Publication Data
US 2023/0181158 A1 Jun. 15, 2023

Related U.S. Application Data

(60) Provisional application No. 62/814,038, filed on Mar. 5, 2019.

(51) Int. Cl.
*A61B 8/00* (2006.01)
*A61B 5/00* (2006.01)

(52) U.S. Cl.
CPC .......... *A61B 8/4416* (2013.01); *A61B 5/0073* (2013.01); *A61B 8/4483* (2013.01); *A61B 2562/12* (2013.01)

(58) Field of Classification Search
CPC .... A61B 8/4416; A61B 8/0858; A61B 8/4483
See application file for complete search history.

(56) References Cited

U.S. PATENT DOCUMENTS 10,631,764 B2   4/2020  Ueda et al.
2003/0109775 A1 6/2003  O'Neil et al.
(Continued)

FOREIGN PATENT DOCUMENTS

JP  2007-521072 A       8/2007
JP  2015-217012 A      12/2015
WO  WO 2018/053017 A1   3/2018

OTHER PUBLICATIONS

Chapter 11—Diffuse Optical Tomography, Biomedical Optics: Principles and Imaging, ISBN 978-7-312-03768-9, pp. 230-234 (with English translation), as cited in an Office Action issued Mar. 2, 2024 in Chinese Patent Application No. 202080034046.9 (not provided), 11 pages.

(Continued)

*Primary Examiner* — Gerald Johnson
(74) *Attorney, Agent, or Firm* — Oblon, McClelland, Maier & Neustadt, L.L.P.

(57) ABSTRACT

A portable two-mode probe to be applied against a biological tissue to be examined, the probe including an ultrasonic transducer configured to emit ultrasonic waves into the tissue and to receive ultrasonic waves reflected by the tissue, the transducer extending along a transverse axis; and at least two optodes placed on either side of the transverse axis, such (Continued)

that the transducer extends between the two optodes. Further, each optode includes a casing containing a light emitter configured to emit a light wave toward the tissue, and/or an optical detector configured to detect a light wave scattered by the tissue. The optodes are arranged such that at least one light emitter and at least one optical detector are placed on either side of the transducer, and at least one optical detector has a detection area formed from a semiconductor and connected to a circuit board.

18 Claims, 7 Drawing Sheets

(56) References Cited

U.S. PATENT DOCUMENTS

| | | |
|---|---|---|
| 2004/0199063 A1 | 10/2004 | O'Neil et al. |
| 2004/0259270 A1 | 12/2004 | Wolf |
| 2006/0276700 A1 | 12/2006 | O'Neil et al. |
| 2012/0184831 A1 | 7/2012 | Seetamraju et al. |
| 2013/0178725 A1 | 7/2013 | O'Neil et al. |
| 2014/0135600 A1 | 5/2014 | O'Neil et al. |
| 2014/0171766 A1 | 6/2014 | Ferris |
| 2017/0049417 A1 | 2/2017 | Liu et al. |
| 2019/0150749 A1* | 5/2019 | Harris ................ A61B 5/0095 |
| 2019/0336057 A1* | 11/2019 | Alford ............... A61B 5/14553 |

OTHER PUBLICATIONS

International Search Report issued on Sep. 1, 2020 in PCT/FR2020/050423 filed on Mar. 3, 2020, 2 pages.

* cited by examiner

ART ANTERIEUR

BIMODAL ULTRASONIC PROBE COMPRISING AN OPTICAL DEVICE FOR DIAGNOSIS

TECHNICAL FIELD

The invention relates to a probe combining an optical modality and an ultrasound modality for diagnosis in vivo of biological tissues, and to the application of such a probe to detection and analysis of cancerous tumors.

PRIOR ART

One of the objectives of medical diagnostics is to increase sensitivity and specificity in order to decrease the number of false positives, while not missing any true positives. Such an objective may be achieved by combining various measurement techniques. This is for example the case when a PET scanner (PET standing for positron emission tomography) and an MRI scanner (MRI standing for magnetic resonance imaging) are combined to improve the characterization of a biological tissue. Ultrasound, combined with optical measurements, also allows the characterization of tissues to be improved. These modalities may be integrated into simple and inexpensive devices, with a view to applications related to point-of-care testing.

As regards optical measurements, the use of optical fibers in a probe, the fibers extending a central unit comprising light sources and/or optical detectors, has already been described in the prior art. For example, patent application US20140187958A1 describes a diagnostic probe intended for an endocavity use, comprising an ultrasound transducer and a series of optical fibers for characterizing fluorescence. The use of optical fibers is accompanied by the following drawbacks:
- a low collection area, and limited numerical aperture;
- attenuation and distortion of the signal;
- decreased flexibility, and robustness affected by the cable connecting the probe to the central unit.

Photoacoustic detection is not a two-mode approach. This method is based on an emission of a light pulse into a tissue, the latter converting it into ultrasonic waves. In most cases, the devices combine conventional ultrasound-imaging and photoacoustic-imaging techniques. Tomowave Labs (Houston—Texas—USA) has for example developed a measuring device for breast cancer based on photoacoustic imaging. See also US20130190595A1. In this device, the breast of a patient is placed in a receptacle. An ultrasound transducer and optical components perform a scan around the receptacle. The main drawback is that such a device is not portable and is not designed for point-of-care testing applications.

FIG. 1 schematically shows a prior-art DOT measuring device (DOT standing for diffuse optical tomography). It comprises a light emitter 31 and an optical detector 32 that are oriented toward a region of interest of the body 40 of a patient, and that are placed in contact with the skin 41 of the patient.

The light emitter 31 generates photons, the latter being absorbed or scattered depending on the composition of the examined tissue. The optical properties of a tumor 43 are generally slightly different from those of the surrounding tissue 42, this allowing the tumor to be located. Some of the scattered photons are collected by the optical detector. The latter is, preferably, a single-photon detector (or single-photon counter) having a high sensitivity over a large detection area. The dashed lines 44 represent the average path length of scattered photons through the tissue 40 and the tumor 43, said photons being detected by the optical detector 32.

When it is desired to analyze the composition of the tumor 43, an optimal configuration is obtained when the emitter 31 and the detector 32 are placed symmetrically with respect to the tumor 43. The penetration depth z of the average path length of the photons may be adjusted by decreasing the distance between the emitter 31 and the detector 32, and/or by inclining them with respect to a direction normal to the plane formed by the surface of the skin 41. Emitter/detector pairs, positioned in other locations, allow a tomographic reconstruction of the examined tissue to be generated.

Use of single-photon optical detectors allows measurements to be taken in the time domain. This allows photons that have propagated through the tissue to be detected as a function of their time-of-flight (TOF). This has two substantial advantages: information is obtained on the average depth of the detected photons in the tissue, and a better discrimination is obtained between absorption and scatter of light in the tissue. Since the relative positions of the emitter and of the detector, and the wavelength, are known, it is possible to determine biological properties of the measured tissue, such as oxygenation, structure, lipid concentration, etc. Determining such biological properties, in combination with the geometry of the tumor (which is obtained by ultrasound imaging), increases the specificity and selectivity with which malignant tumors may be screened.

SUMMARY OF THE INVENTION

One subject of the invention is a portable probe, combining an ultrasound modality and an optical modality, such as described in the appended claims. More precisely, the probe may comprise:
- an array of ultrasonic transducers, which array is configured to generate an ultrasonic image, for example a phase image, a Doppler image, an elastograph;
- at least one light source such as a laser emitter or a light-emitting diode (LED);
- an optical detector and electronic modules configured to drive the components of the probe and process the signal.

The optical modality of the invention is based, or may be based, on diffuse optical tomography. The optical measurements taken for the diffuse optical tomography, combined with the ultrasonic modality, allow improved indicators of the physiological or pathological state of the examined tissue to be obtained. Thus, the invention allows improved diagnostics, with a better specificity and a better sensitivity. This is particularly advantageous when screening and characterizing cancer.

The combination of ultrasonic and optical modalities requires a superposition of their respective fields of observation. To this end, one subject of the invention is a process for setting the position of each component of a two-mode portable probe. One particular aspect of the invention is that the ultrasonic probe is placed between at least one light emitter and one optical detector. Another particular aspect relates to the use of optical measurements in a time-domain approach. On the basis of this type of measurement, a reconstruction of the examined tissue is generated on the basis of a temporal distribution of times of detection of photons having propagated through the tissue. This allows a quantitative analysis of reduced scattering coefficients and absorption coefficients in the tissue. This results in a better definition of the volume of a tumor present in the tissue.

Another subject of the invention is a process for manufacturing a two-mode probe, according to the appended process claims.

The invention will be better understood on reading the description of the examples of embodiments, which are described, in the rest of the description, with reference to the figures listed below, the latter not limiting the scope of the claims.

FIGURES

FIG. 3 allows the main directional axes to be defined.

Figure 9:
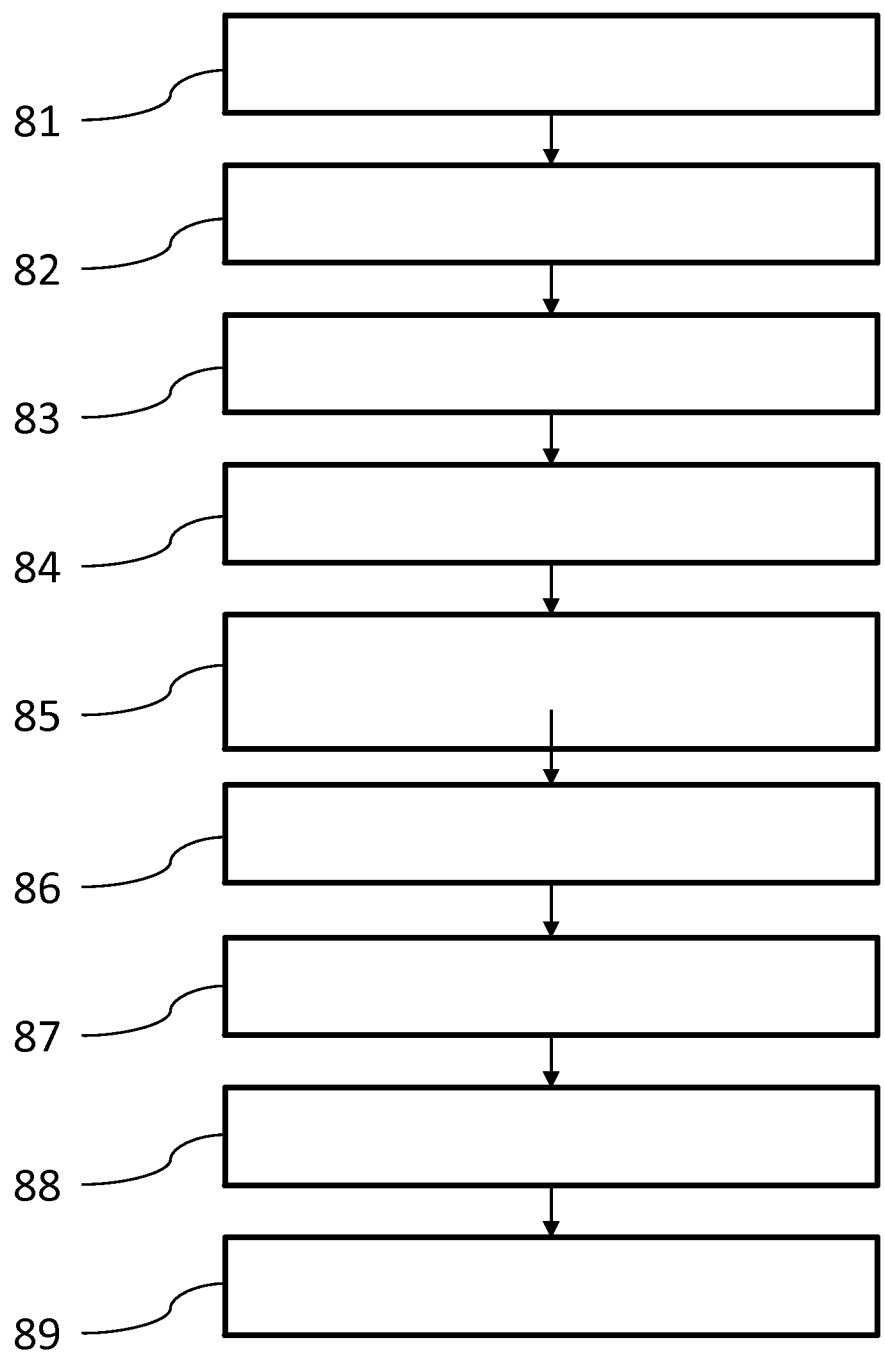

FIG. 9 describes the main steps of a process for assembling components forming a two-mode ultrasound/optical probe.

DESCRIPTION OF PARTICULAR EMBODIMENTS

The present invention relates to a two-mode probe, combining ultrasonic (US) imaging and optical measurements for obtaining biological parameters in the context of screening for cancerous tumors. More precisely, the optical modality is based on diffuse optical tomography (DOT).

Figure 1:
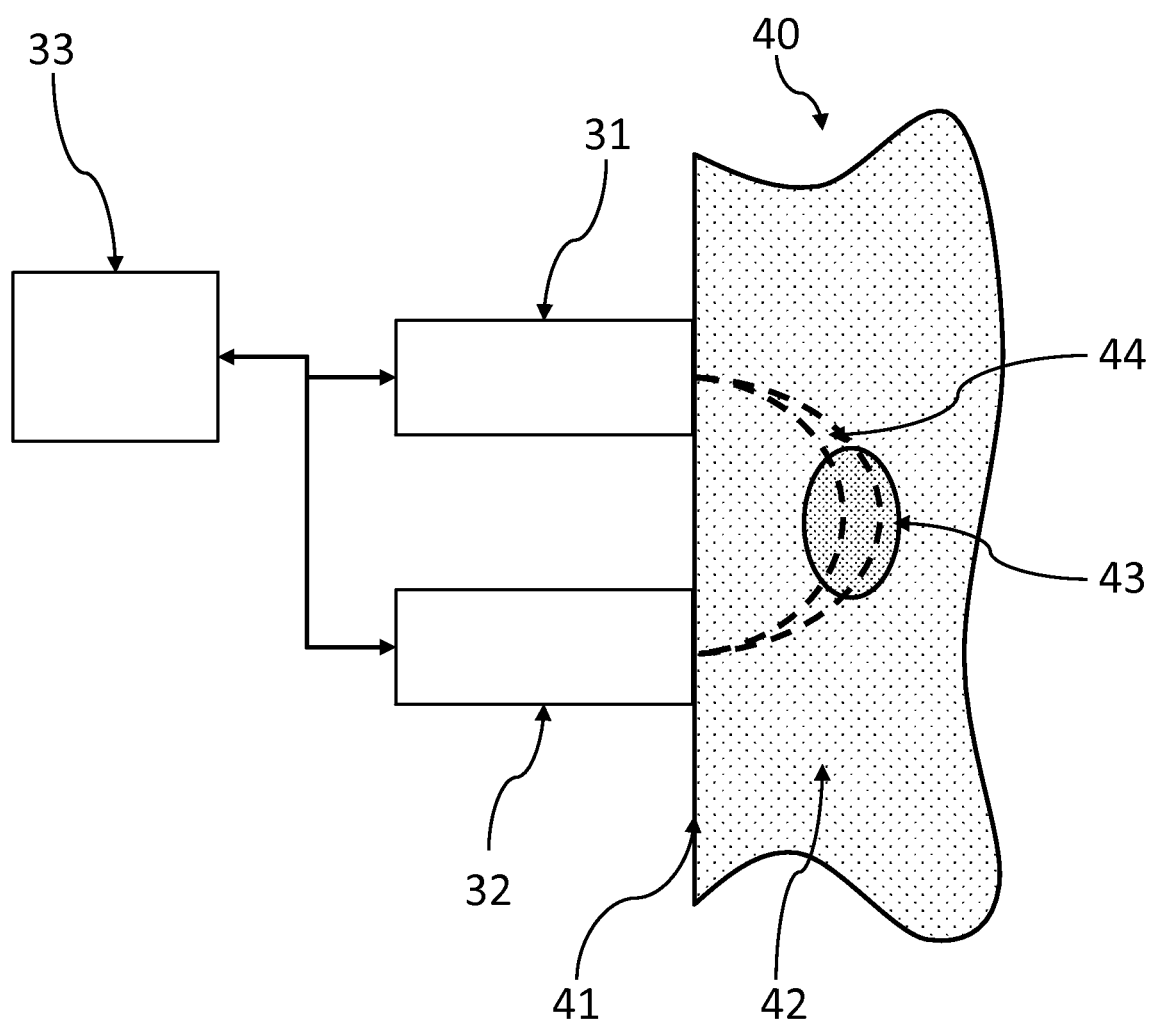
FIG. 1 is a schematic illustration of a diffuse-optical-tomography (DOT) system.
Figure 2:
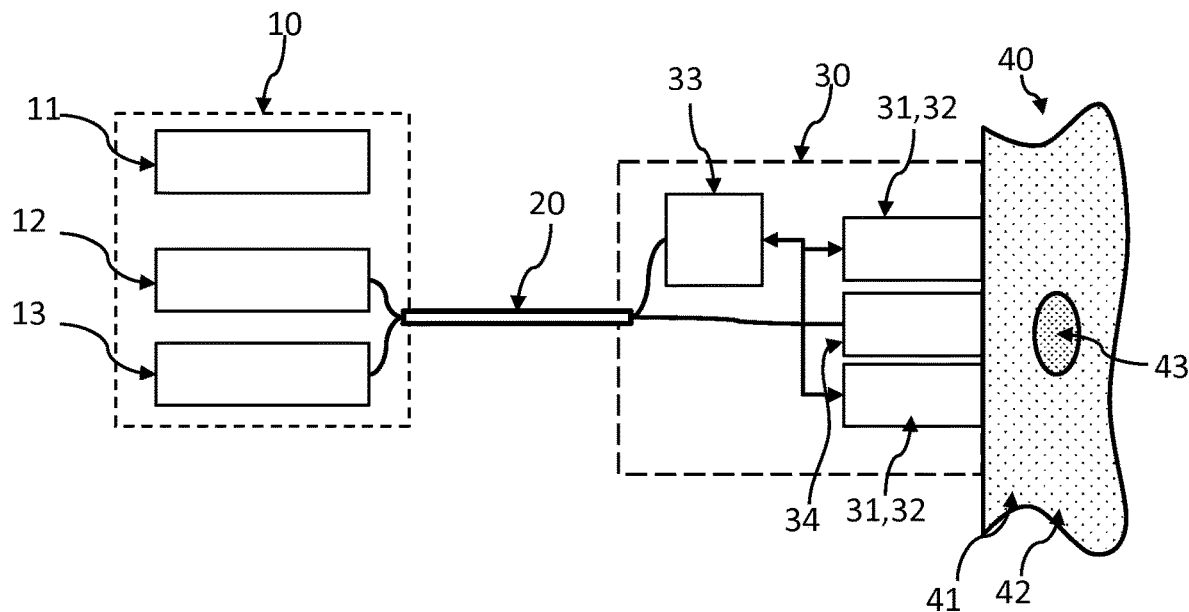
FIG. 2 is a functional schematic of an example of a system combining ultrasonic (US) and diffuse-optical-tomography (DOT) modalities.

FIG. 2 shows an example of a device comprising a two-mode probe 30 electrically connected to a main unit 10 via a plurality of electrical wires assembled into the same cable 20.

The weight and size of the probe 30 are such that it may be carried by hand and manipulated so as to be placed in contact with the body of a patient 40, and oriented toward a region of interest, and more particularly a tumor 43 to be examined. A coupling gel is generally applied to the interface between the probe and the analyzed body, so as to facilitate a propagation of the ultrasonic waves through the interface. The gel may also have optical properties, for example absorption properties, in order to prevent crosstalk between the optical components. As regards the optical modality, the probe comprises optodes, each optode comprising a light emitter 31 and/or optical detector 32. The components 31 and 32 of a given optode are electrically connected to a drive circuit 33. The latter is configured to deliver electrical power signals, or synchronization signals, and to convert the detected signal into digital data. A two-way link connects the optical drive circuit 33 to an optical processing unit 12, through a cable 20. The probe 30 also comprises an ultrasonic transducer 34, formed from elementary ultrasonic transducers, which converts electrical signals, which originate from an ultrasonic processing unit 13, into ultrasonic acoustic waves. The latter are emitted toward the body 40. The ultrasonic transducer 34 also converts ultrasonic waves, reflected by the body 40, into electrical signals, which are intended to be processed by the ultrasonic processing unit 13. In the ultrasonic transducer, the elementary ultrasonic transducers are preferably aligned along a transverse axis parallel to an axis X described with reference to FIG. 3.

The main unit 10 comprises a user interface 11, which allows the optical processing unit 12 and the ultrasonic processing unit 13 to be controlled. The optical processing unit 12 and the ultrasonic processing unit 13 produce an electrical signal intended to control the components of the probe. They also allow the signals measured by the probe to be processed so as to deliver information that is exploitable by a user.

Figure 3:
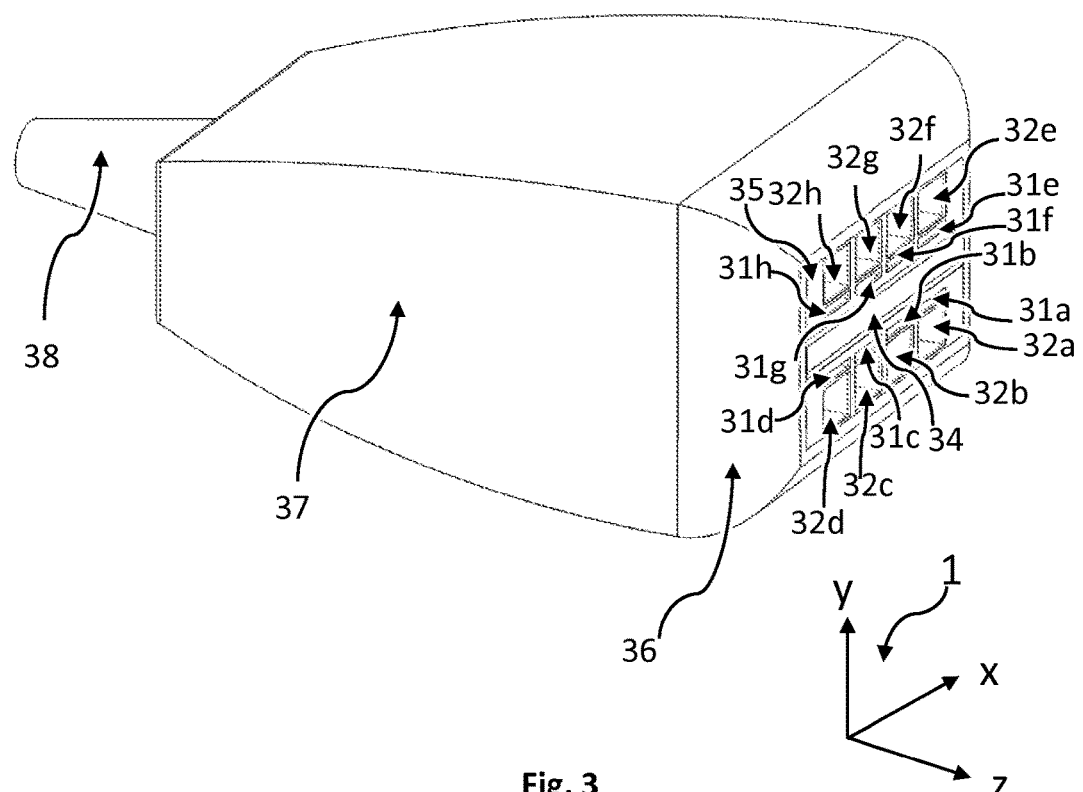
FIG. 3 is a perspective view of one embodiment of a portable two-mode probe.

In FIG. 3 a coordinate system 1 has been shown, with a view to clarifying the description. The coordinate system 1 defines a (depthwise) longitudinal direction Z, which points toward the body 40, an elevation direction Y and an azimuthal direction X.

Figure 4:
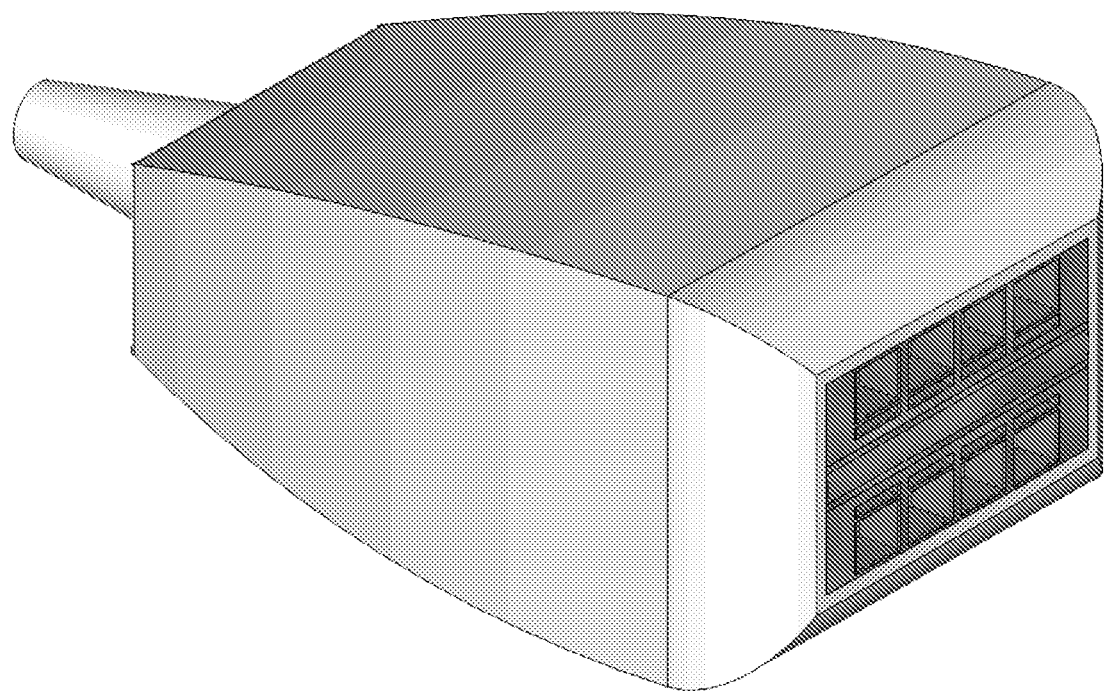
FIG. 4 is a perspective view that is similar to FIG. 3, showing a shaded representation.

As shown in FIGS. 3 and 4, in one preferred embodiment, the probe 30 comprises a far end 35, which is intended to be applied against the skin 41 of the patient. The far end is confined in a front cover 36, which forms a nose of the probe 30. The front cover 36 extends a central cover 37. The latter is extended by a hollow joint 38, into the interior of which the cable 20 is inserted. The far end 35 comprises input/output interfaces of the ultrasonic transducer 34, of the light emitter 31, and of the optical detector 32. In the preferred embodiment, the probe 30 comprises a plurality of light emitters 31a . . . 31h and a plurality of optical detectors 32a . . . 32h. Preferably, at least one light emitter 31a and at least one optical detector 32a are placed in an optode, as described with reference to FIG. 3. The optical detectors 32a . . . 32h have a large detection area. The detection area of a detector corresponds to the area of a sensitive component of said detector. Thus, each optical detector 32a . . . 32h comprises a detection area each side of which preferably extends over a width larger than 0.5 mm, or even 5 mm. The detection area is typically larger than 5×5 mm$^2$, and may for example be 10×10 mm$^2$. Each light emitter may comprise a plurality of elementary light emitters, which may, for example, emit light at various wavelengths. Each elementary light emitter may be a laser diode or a light-emitting diode. The detection area of at least one detector, or even of each detector, is larger than the emission area of each emitter.

Each light emitter is preferably configured to emit a light pulse. In the case of a time-domain optical measurement, the duration of the pulse is shorter than a few tens of picoseconds (ps), and for example shorter than 50 ps or than 10 ps (FWHM: full width at half maximum). A light emitter may for example be a pulsed laser diode.

The emitters and detectors define, two-by-two, emitter/detector pairs. The emitter/detector pairs 31a/32a, 31b/32b . . . 31h/32h are placed on either side of the acoustic transducer 34. The distance between the emitter and detector 31a/32a, 31b/32b . . . of a given optode is preferably comprised between 1 mm and 20 mm and for example of the order of 7 mm. This allows a measurement of the optical properties of a tumor located in proximity to the skin, i.e. at a depth smaller than 5 cm, and for example comprised between 0 cm and 5 cm, to be obtained. In the elevation direction Y, the far end 35 comprises in succession:

- a row with 4 optical detectors 32a . . . 32d,
- a row with 4 light emitters 31a . . . 31d,
- the ultrasonic transducer 34;
- a row with 4 light emitters 31e . . . 31h,
- a row with 4 optical detectors 32e . . . 32h.

The emitters and detectors are respectively aligned parallel to the direction X, in which direction the ultrasonic transducer extends, and are placed on either side of the latter. As a result, the observation field of the ultrasonic imaging modality is superposed with the observation field of the diffuse optical imaging modality. The ultrasonic transducer 34 is bounded by a perimeter. The distance between each optical detector and the perimeter may be comprised between 0.5 mm and 20 mm.

A protective material fills the rest of the far end. The protective material may be a silicone rubber, or any other curable or polymerizable biocompatible material, such as described with reference to FIGS. 7A to 7C. When the ultrasonic transducer 34 spans, in the elevation direction Y, a height of 5 mm, the space between the transducer and the closest rows of optical components (detectors or emitters of light) spans, in the direction Y, a distance of approximately 1 mm. Such a configuration allows an overlap of the respective observation fields of the optical modality and of the acoustic transducer. Each observation field corresponds to an image formed in a plane parallel to the axes X and Z. In addition, such a configuration allows an emitter/detector pair comprising an optical emitter 31a of an optode and an optical detector 32b, 32c, 32d, 32e, 32f, 32g and 32h of a different optode to be used, the emitter and detector being spaced apart along the axis X and/or the axis Y. Thus, the probe allows emitter/detector pairs to be defined in which the axis connecting the emitter to the detector is inclined with respect to the elevation axis Y, or the azimuthal axis X, in the XY-plane. This makes it possible to vary the distance between the emitter and the detector between a minimum value, such as described above (between 1 mm and 20 mm, 7 mm for example), and a maximum value, the latter being of the order of 30 to 80 mm, and for example 40 mm, or 60 mm, for the furthest apart emitter/detector pairs. Placing the ultrasonic sensor between the emitter and the detector also allows an overlap of the respective fields of observation of the optical modality and of the optical transducer. The combination of various emitter/detector distances allows measurements to be combined with a view to generating a tomographic reconstruction.

It will be understood from the above that a plurality of optical detectors may be used to measure scattered photons emitted by the same light emitter.

Holding the Components in the Probe

Figure 5:
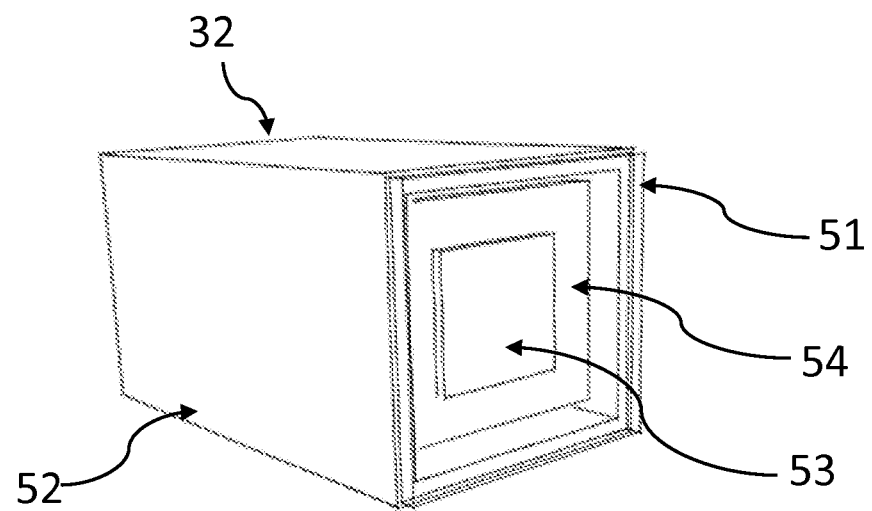
FIG. 5 is a perspective view of an example of an optode comprising a single-photon detector having a large detection area.

FIG. 5 shows a preferred embodiment, in which an optode comprises an optical detector 32, the latter comprising a sensitive component 53, i.e. a component that is sensitive to light. The optical detector 32 is preferably a single-photon detector (or a single-photon counter).

The sensitive component 53 is connected to a printed circuit board 54 (PCB), the latter allowing the sensitive component 53 to be held mechanically, and the sensitive component 53 to be connected electrically. The electrical connections of the PCB 54 may be extended to the optical drive circuit 33 (see FIG. 2), using a flexible printed circuit board or electrical wires.

The sensitive component 53 is placed set back, with respect to a front face of a casing 52. The casing 52 is preferably made from a metal, so as to allow the components to be shielded electrically, and to allow a rigid mechanical attachment to be achieved. The front face of the casing 52 is intended to be placed between the sensitive component 53 and the examined tissue. The front face of the casing 52 delineates an aperture, which is intended to allow light to pass. In order to avoid a direct contact between the sensitive component 53 and the skin, which would lead to a risk of contamination, the aperture is closed by an optically transparent plate 51. The plate 51 may be made of glass, or of polymer, or of any other material that is transparent to the optical wavelengths employed for the diffuse optical measurements. The transparent plate 51 is joined to the casing 52 and may protrude from the front face of the latter. The dimensions of the transparent plate 51, in the azimuthal and elevation directions, are smaller than the dimensions of the casing. The thickness of the transparent plate 51 may vary between 0.4 mm and a few millimeters. Another aperture, not shown in FIG. 5, is formed in another face of the casing 52 in order to allow electrical connections.

The casing 52 and the various elements that it encloses, which were described in the preceding paragraph, is designated by the term "optode". The optode preferably comprises one or more optical emitters 31. It may for example be a question of one or more light-emitting diodes or of one or more laser sources. An optode may comprise optical emitters that emit at various wavelengths. An optode may also comprise an electronic acquiring circuit, so as to measure variations in the light backscattered by the examined tissue, i.e. that has propagated through the examined tissue. Preferably, the acquiring circuit allows time-domain measurements of photons backscattered by the examined tissue and detected by the optical detector 32 of the optode to be taken. It is for example a question of establishing a time-domain distribution of the photons detected by the optical detector 32, or of the parameters of such a distribution. Thus, an optode is a unitary component comprising an optical detector 32 and/or a light emitter 31 and/or an acquiring circuit connected to the optical detector 32.

Figure 6:
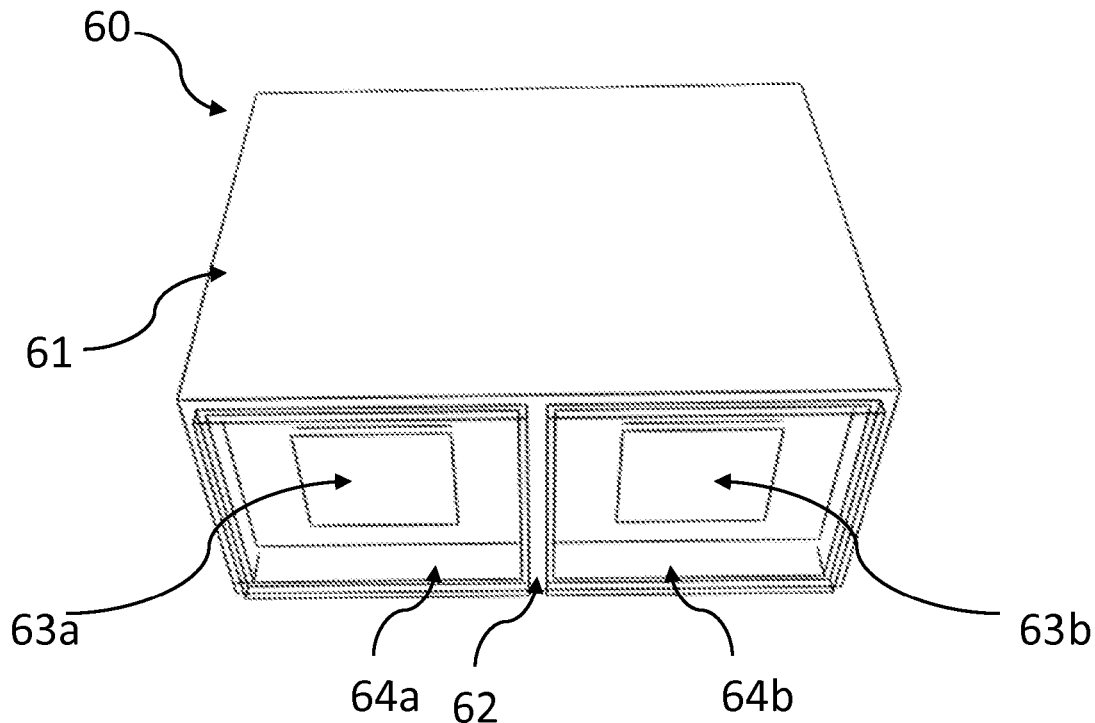
FIG. 6 is a perspective view of another embodiment, comprising two optodes associated in the same casing.

FIG. 6 shows another example of an embodiment of an optode, in which two sensitive components 63a, 63b are grouped together in the same casing 61. The casing 61 comprises an internal metal wall, placed between each optical component, so as to prevent crosstalk. The optical component comprises transparent plates 64a and 64b that are separated from each other by a free space 62. The free space between the two transparent plates allows the two plates to be isolated optically. The free space between the two transparent plates spans a distance comprised between 1 mm and 3 mm, or between 0.5 mm and 20 mm.

The embodiment described with reference to FIG. 6 comprises, nonlimitingly, two optical detectors. The invention encompasses optodes comprising casings, such as described above, comprising optical detectors, or a combination of at least one optical detector and of optical emitters, placed in the same casing.

Figure 7A:
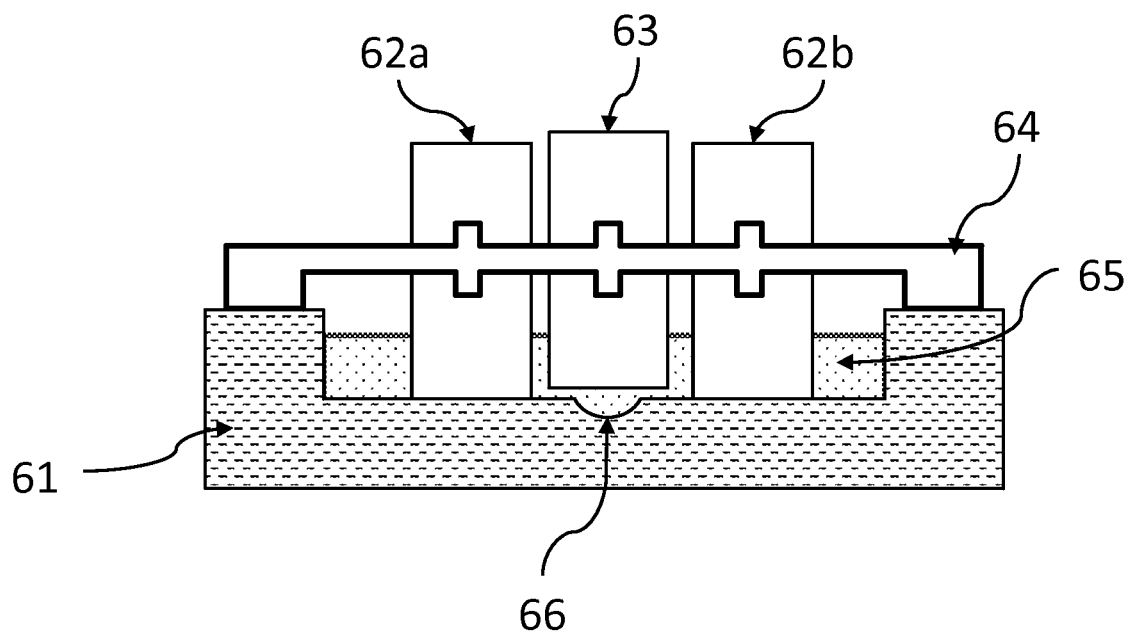
FIG. 7A is a schematic showing a section, seen from the side, of one embodiment relative to holding an ultrasonic transducer and optodes in a molded portion, so as to form a protective far end comprising an ultrasonic acoustic lens.
Figure 7B:
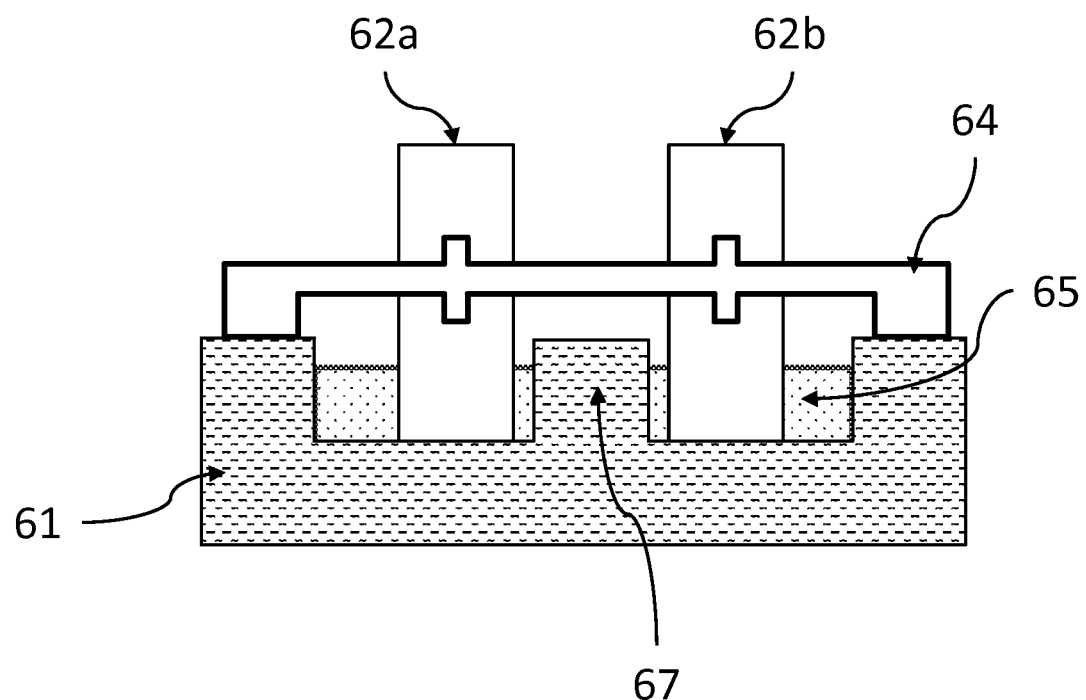
FIG. 7B is a schematic showing a section, seen from the side, of another embodiment relative to holding ultrasonic transducers and optodes in a molded portion. According to this embodiment, the mold forms an aperture allowing a US transducer confined in its own protective jacket to be inserted.
Figure 7C:
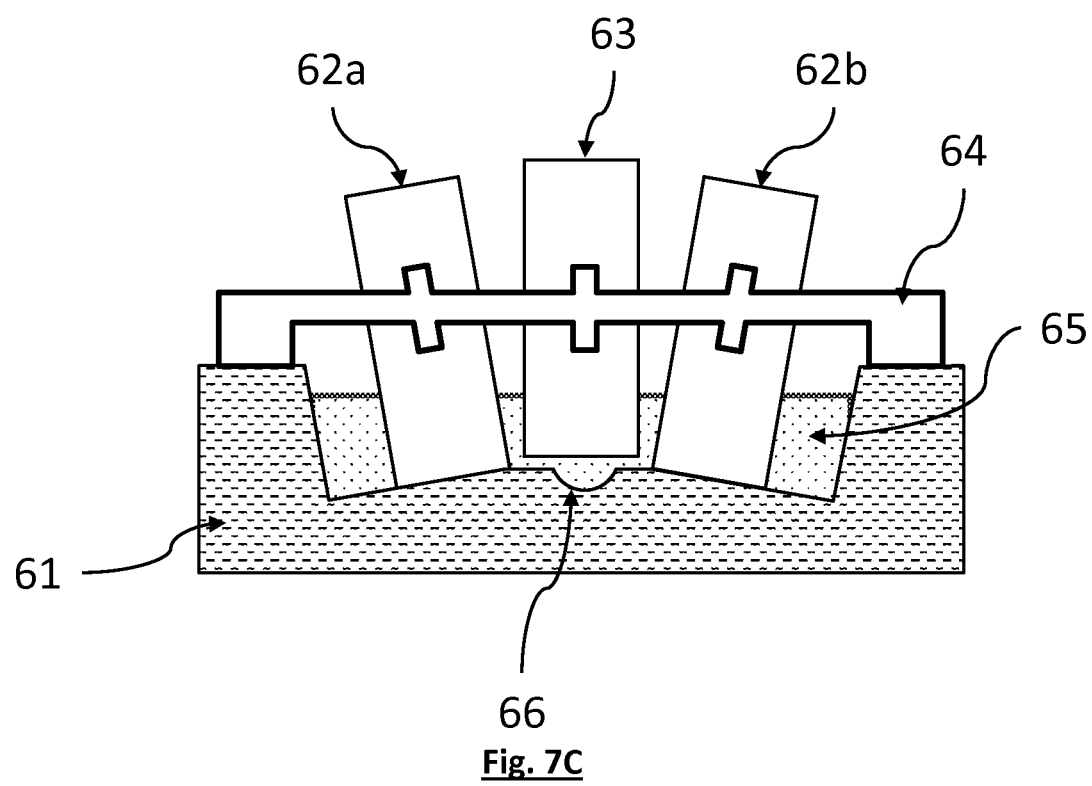
FIG. 7C is a schematic showing a section, seen from the side, of another embodiment in which the optodes are inclined with respect to a longitudinal direction of the probe.

FIGS. 7A, 7B and 7C show sections, seen from the side, of one embodiment allowing an ultrasonic transducer 63 and optodes 62a and 62b, such as described above, to be rigidly fastened in place, and a protective material 65 to be applied to the far end. The protective material 65 may be a polymer, for example a silicone rubber, or another biocompatible material. The protective material may be prepared in the liquid phase, then poured into a mold 61. After the solidification of the material 65 by polymerization, the mold 61 is removed. The ultrasonic transducer 63 and the optodes 62a and 62b are placed in their final position, and securely held by two flanges 64, on two of their lateral sides. In FIG. 7A, only a single flange 64 may be seen. The components 62a, 62b and 63 may be fastened to each flange by screwing, adhesive bonding, or another joining means. During the molding operation, the flanges are temporarily screwed to the mold 61, so as to keep the external surfaces of the transparent plates of the optodes 62a and 62b in contact with the bottom of the mold 61.

In FIG. 7A, an ultrasonic transducer 63 has been shown set back with respect to the ends of the optodes 62a and 62b. The surface of the bottom of the mold 61 comprises a semicylindrical cavity 66, which extends around an axis parallel to a transverse axis of the transducer, in the present case the axis X. The length of the cylindrical cavity 66 corresponds to the entire length of the ultrasonic transducer (i.e. all of the elementary ultrasonic transducers) in the transverse direction X. The semicylindrical cavity 66 is filled with the silicone rubber or any other material having the same acoustic characteristics. The semicylindrical cavity 66 then forms an acoustic lens. The distance between the external surface of the transducer 63 and the apex of the cavity 66 is typically comprised between 1 mm and 2 mm. The acoustic lens formed forms a protuberance, which protrudes from the far end by a distance generally smaller than 1 mm. When the material 65 has solidified, the assembly comprising the ultrasonic transducer 63, the optodes 62a and 62b, the flange 64 and the molded material 65, is removed from the mold in order to be placed in a cavity formed in the front cover 36 of the probe, the front cover forming a nose. The flange is then fastened to the front cover 36.

FIG. 7B shows another embodiment of an assembling process. According to this embodiment, the mold comprises a recess 67. The recess 67 defines an area, inside the mold, corresponding to the area of an acoustic transducer having been covered beforehand with a protective jacket that is specific thereto. After the material 65 has solidified, the assembly comprising the optodes 62a, 62b, the flange 64 and the molded material 65, is removed from the mold. The recess 67 allows a hollow cavity to be formed in the molded material, between the optodes 62a and 62b. The process comprises an additional step of introducing the transducer 65 into the hollow cavity formed beforehand in the polymerized material. After the US transducer has been inserted into the hollow cavity, it may be mechanically attached to the flange 64 holding the optodes 62a and 62b. Such an embodiment is preferred, because it allows the transducer to be integrated after testing thereof beforehand.

FIG. 7C shows an embodiment similar to the embodiment shown in FIG. 7A. The optodes 62a and 62b are inclined with respect to the longitudinal axis Z, which corresponds to the longitudinal axis of the US transducer. The angle of inclination may for example reach 20°. Such a configuration is particularly suitable for the configuration in which a cancerous tumor, or any other region of interest, is included in a body part of rounded shape, for example a breast or the neck.

Figure 8:
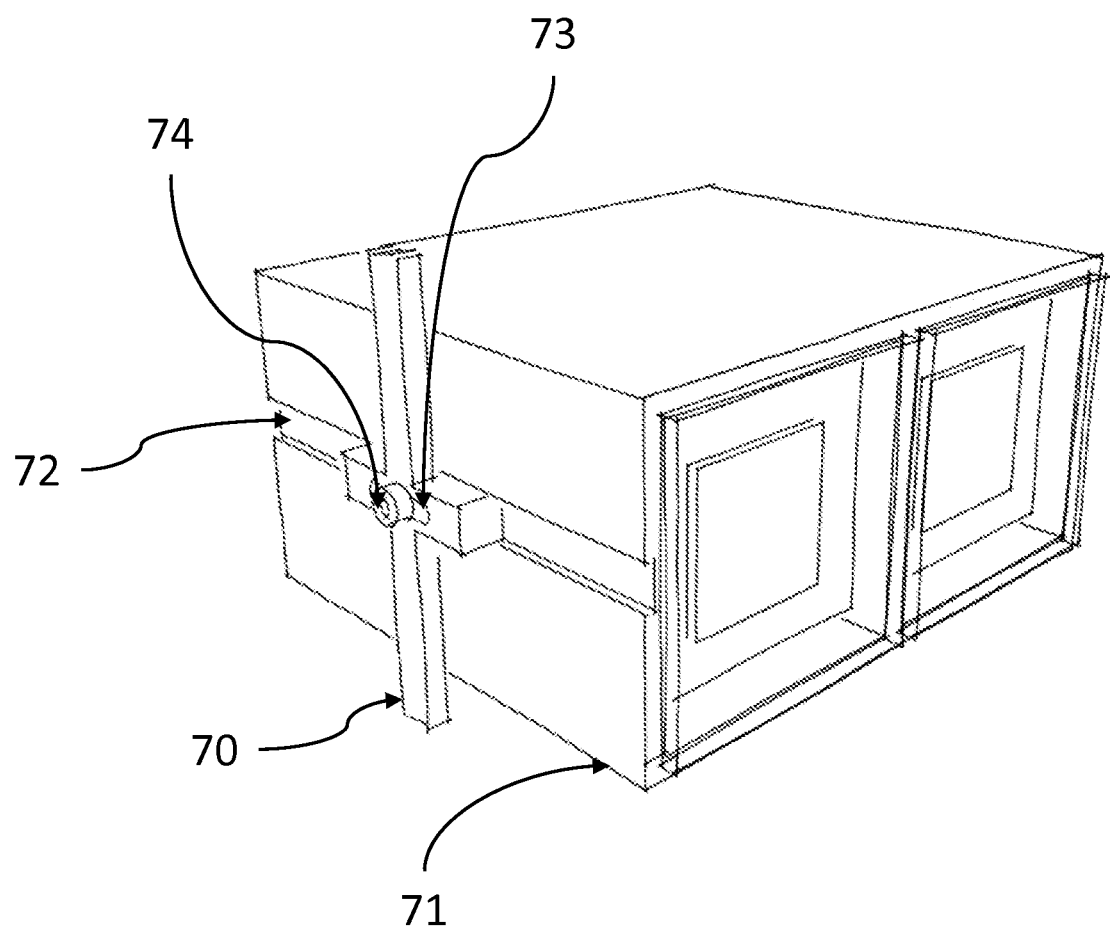
FIG. 8 is a perspective view of an example of a fastening flange, allowing an optode to be held.

FIG. 8 is a perspective view of a preferred embodiment in which a flange 70 is joined to an optode 71. A groove 72 extends over a lateral face of the optode 71, parallel to the longitudinal axis Z, i.e. perpendicular to the front face. The cross section of the groove may describe various shapes, for example a square, a rhombus or a rounded section. The flange 70 comprises an extension segment, which extends parallel to the longitudinal axis Z, parallel to the groove 72. The flange 70 also comprises a protuberance allowing a mechanical link with the optode to be ensured. The shape of the protuberance may vary, depending on the cross section of the groove 72, such that the flange is able to slide along the groove, along the longitudinal axis Z, the protuberance being engaged in this groove. The flange is held stationary in the elevation direction Y. The flange 70 is fastened to the optode by way of a screw 74. A through-aperture 73, of oblong shape, is produced in the flange, so as to be able to make possible an adjustment of a position of the optode in the longitudinal direction. A second flange is similarly fastened to an opposite lateral face of the optode 71. Thus, all the degrees of freedom are constrained, with the exception of a slight adjustment of the translation of the optode in the longitudinal direction Z. The adjustment, in the longitudinal direction, allows precise positioning of the front faces of the optodes, and of any ultrasonic transducer, at the desired position. When the front faces of the optodes are placed slightly set back with respect to the bottom of the mold, a thin layer of protective material is able to get between the front faces and the bottom of the mold. This thin layer must preferably be removed at the end of the molding. When all the components, held by the flange, are positioned as desired, the screw 74 (or other fastening means) is tightened.

FIG. 9 illustrates the main steps of a process, such as described above, for manufacturing a far end of a probe, it being understood that the obtainment of a complete probe assumes other manufacturing steps. The manufacture of the probe comprises certain steps 81 to 89 listed below. Step 82 relates only to the embodiment described with reference to FIGS. 7A and 7C. The assembling step 88 relates only to the embodiment described with reference to FIG. 7B.

Step 81: assembling the optodes with the flanges;
Step 82: assembling the ultrasonic transducer with the flanges;
Step 83: positioning the optodes and the ultrasonic transducer then tightening the screws;
Step 84: placing the assembled optodes in the mold, and temporarily fastening the mold to the flanges;
Step 85: filling the mold with a biocompatible protective material, for example a polymer, and polymerizing it;
Step 86: removing the mold;
Step 87: inserting the assembly, coated with the protective polymer, into the cover of the probe;
Step 88: inserting the ultrasonic transducer into the hollow cavity produced in the polymer.
Step 89: fastening the assembly to the front cover of the probe.

The invention claimed is:

1. A portable two-mode probe to be applied against a biological tissue to be examined, the probe comprising:
   an ultrasonic transducer configured to emit ultrasonic waves into the tissue and to receive ultrasonic waves reflected by the tissue, the transducer extending along a transverse axis; and
   a plurality of optodes arranged on either side of the transverse axis, such that the ultrasonic transducer extends between the optodes, each optode comprising a casing, the casing containing a light emitter configured to emit a light wave toward the tissue, and/or an optical detector configured to detect a light wave scattered by the tissue, wherein the plurality of optodes are arranged such that at least one light emitter and at least one optical detector are placed on either side of the ultrasonic transducer;

the probe further comprises at least one optical detector having a detection area formed from a semiconductor and connected to a circuit board; and the probe includes a plurality of light emitters and a plurality of optical detectors, the probe being configured such that distances between an optical detector and light emitters varies between 1 mm and 80 mm.

2. The two-mode probe as claimed in claim 1, wherein at least one optode, of the plurality of optodes, comprises at least one light emitter configured to emit a light wave into the tissue, and one optical detector configured to detect a light wave scattered by the tissue.

3. The two-mode probe as claimed in claim 2, wherein at least one light emitter is a laser diode or a light-emitting diode.

4. The two-mode probe as claimed in claim 1, wherein an optode, of the plurality of optodes, comprises a plurality of light emitters, each light emitter being configured to emit light at a different wavelength from another light emitter of the optode.

5. The two-mode probe as claimed in claim 1, wherein at least one optical detector is connected to an acquiring circuit board configured to count photons detected as a function of time.

6. The two-mode probe as claimed in claim 1, wherein an optode, of the plurality of optodes, is housed in a casing, the casing comprising a front face defining an aperture, the detection area being placed set back with respect to the front face, the aperture allowing light to be transmitted to the optode or from the optode.

7. The two-mode probe as claimed in claim 6, wherein an optode, of the plurality of optodes, comprises a transparent plate, extending through the aperture, such that when the two-mode probe is applied against the tissue, the transparent plate is placed in contact with the tissue.

8. The two-mode probe as claimed in claim 7, wherein an optode, of the plurality of optodes, comprises a plurality of optical detectors, emerging set back from a given front face, the front face defining an aperture, the optode comprising as many transparent plates as optical detectors, each transparent plate being placed away from another transparent plate.

9. The two-mode probe as claimed in claim 8, wherein a distance between two transparent plates of a given optode is larger than 0.5 mm and smaller than 1 mm.

10. The two-mode probe as claimed in claim 1, comprising a plurality of light emitters and a plurality of the optical detectors, wherein:

the light emitters are aligned parallel to the transverse axis; and the optical detectors are aligned parallel to the transverse axis.

11. The two-probe as claimed in claim 10, wherein the light emitters and/or the optical detector are arranged in a matrix array.

12. The two-mode probe as claimed in any claim 1, wherein an optode, of the plurality of optodes, is housed in a casing, the casing comprising a front face defining an aperture, the aperture allowing a transmission of light to the optode or from the optode, and wherein the casing comprises a lateral face, perpendicular to the front face, the lateral face comprising a groove extending perpendicular to the front face.

13. The two-mode probe as claimed in claim 12, wherein each optode, of the plurality of optodes, is kept securely fastened to the ultrasonic transducer by a flange, the flange being fastened to at least two optodes placed on either side of the ultrasonic transducer, by a fastening means engaged in the groove of each thereof.

14. The two-mode probe as claimed in claim 13, wherein the fastening means permits an adjustment of a position of each optode, via translation of the flange, in each groove, by a translation distance between 1 mm and 2 mm.

15. A process for manufacturing the two-mode probe as claimed in claim 12, using optodes comprising a transparent plate extending to the front face, the process comprising:

assembling optodes via a flange, the flange joining two opposite optodes of the assembly, the flange being configured to be translated in grooves produced in the casings of said opposite optodes;

placing the assembly in a mold, the mold comprising a surface forming a bottom, such that the transparent plate of each optode is applied against the bottom of the mold;

filling the mold using a polymerizable biocompatible material, such that the material extends around the assembly;

polymerizing the biocompatible material;

removing the assembly from the mold, such that the biocompatible material forms a jacket around the assembly, the removed assembly forming a far end of the probe;

fastening the far end of the probe to a cover of the probe.

16. The manufacturing process as claimed in claim 15, wherein the bottom of the mold comprises a recess, the recess being formed such that:

when the transparent plate of each optode is applied against the bottom of the mold, the recess lies between at least two optodes;

on removal of the assembly from the mold, the recess of the mold frees a hollow cavity in the biocompatible material;

the process being such that after removal of the assembly, the process comprises inserting an ultrasonic transducer in the hollow cavity, the ultrasonic transducer having been covered beforehand with a protective jacket.

17. The manufacturing process as claimed in claim 15, wherein an ultrasonic transducer is joined to the flanges before the mold is filled, the transducer forming part of the assembly.

18. A portable two-mode probe to be applied against a biological tissue to be examined, the probe comprising:

an ultrasonic transducer configured to emit ultrasonic waves into the tissue and to receive ultrasonic waves reflected by the tissue, the transducer extending along a transverse axis; and at least two optodes arranged on either side of the transverse axis, such that the ultrasonic transducer extends between the at least two optodes, each optode comprising a casing containing a light emitter configured to emit a light wave toward the tissue, and/or an optical detector configured to detect a light wave scattered by the tissue, wherein the optodes are arranged such that at least one light emitter and at least one optical detector are placed on either side of the ultrasonic transducer;

the probe further comprises at least one optical detector having a detection area formed from a semiconductor and connected to a circuit board, and the ultrasonic transducer is bounded by an external perimeter, and a distance between an external perimeter of the ultrasonic transducer and each optical detector is between 0.5 mm and 20 mm.

* * * * *

UNITED STATES PATENT AND TRADEMARK OFFICE
CERTIFICATE OF CORRECTION

| | | |
|---|---|---|
| PATENT NO. | : 12,357,270 B2 | Page 1 of 1 |
| APPLICATION NO. | : 17/436387 | |
| DATED | : July 15, 2025 | |
| INVENTOR(S) | : Tisa et al. | |

It is certified that error appears in the above-identified patent and that said Letters Patent is hereby corrected as shown below:

On the Title Page

Column 1, Item (72), under "Inventors", Line 1, delete "Segrate Mi" and insert -- Segrate, MI --, therefor.

Column 1, Item (72), under "Inventors", Line 2, delete "Serio" and insert -- Serio, --, therefor.

Column 1, Item (72), under "Inventors", Line 5, delete "Joue-Les-Tours" and insert -- Joué-lès-Tours --, therefor.

Column 1, Item (72), under "Inventors", Line 9, delete "Fiorenzuloa d'Arda (PC)" and insert -- Fiorenzuola d'Arda (PC), --, therefor.

Column 1, Item (72), under "Inventors", Line 10, delete "Paruzzaro" and insert -- Paruzzaro (NO), --, therefor.

In the Claims

In Column 8, Claim 1, Line 64, delete "the casing containing" and insert -- containing --, therefor.

In Column 9, Claim 11, Line 55, delete "two-probe" and insert -- two-mode probe --, therefor.

In Column 9, Claim 12, Line 58, delete "in any" and insert -- in --, therefor.

Signed and Sealed this
Twenty-first Day of October, 2025

John A. Squires
*Director of the United States Patent and Trademark Office*